(12) United States Patent
Yang et al.

(10) Patent No.: US 10,056,556 B2
(45) Date of Patent: Aug. 21, 2018

(54) SPACE-THROUGH CHARGE TRANSFER COMPOUND, AND ORGANIC LIGHT EMITTING DIODE AND DISPLAY DEVICE USING THE SAME

(71) Applicant: LG Display Co., Ltd., Seoul (KR)

(72) Inventors: Joong-Hwan Yang, Gwangmyeong-si (KR); Kyung-Jin Yoon, Goyang-si (KR); Hyo-Jin Noh, Paju-si (KR); Dae-Wi Yoon, Paju-si (KR); In-Ae Shin, Paju-si (KR); Jun-Yun Kim, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 114 days.

(21) Appl. No.: 14/954,840

(22) Filed: Nov. 30, 2015

(65) Prior Publication Data
US 2016/0163989 A1 Jun. 9, 2016

(30) Foreign Application Priority Data

Dec. 5, 2014 (KR) .................. 10-2014-0173911
Oct. 15, 2015 (KR) .................. 10-2015-0144199

(51) Int. Cl.
*H01L 51/00* (2006.01)
*H01L 51/50* (2006.01)
(Continued)

(52) U.S. Cl.
CPC ........ *H01L 51/0051* (2013.01); *C07D 239/26* (2013.01); *C07D 249/08* (2013.01); *C07D 251/24* (2013.01); *C07D 403/10* (2013.01); *C09K 11/025* (2013.01); *C09K 11/06* (2013.01); *H01L 27/32* (2013.01); *H01L 51/0059* (2013.01); *H01L 51/0067* (2013.01); *H01L 51/0072* (2013.01); *H01L 51/5012* (2013.01); *H01L 51/5024* (2013.01); *C09K 2211/1007* (2013.01); *C09K 2211/1011* (2013.01); *C09K 2211/1014* (2013.01); *C09K 2211/1044* (2013.01); *C09K 2211/1059* (2013.01);
(Continued)

(58) Field of Classification Search
None
See application file for complete search history.

(56) References Cited

U.S. PATENT DOCUMENTS

2016/0359118 A1* 12/2016 Buchwald ........... H01L 51/0072

FOREIGN PATENT DOCUMENTS

JP 2008-177559 A 7/2008
JP 2010-283003 A 12/2010

OTHER PUBLICATIONS

Machine-assisted English translation of JP2008-177559, as provided by JPO (2008).*
(Continued)

*Primary Examiner* — Sin J Lee
(74) *Attorney, Agent, or Firm* — Fenwick & West LLP

(57) ABSTRACT

Discussed is a space-through charge transfer compound including a paracyclophane core, an electron donor moiety selected from the group consisting of carbazole and diphenyl amine, and an electron acceptor moiety selected from the group consisting of pyrimidine, diphenyltriazine, and triazole. The electron donor moiety and the electron acceptor moiety are indirectly or directly combined to the paracyclophane core with or without a linker, respectively.

16 Claims, 3 Drawing Sheets

(51) Int. Cl.
*H01L 27/32* (2006.01)
*C07D 249/08* (2006.01)
*C07D 239/26* (2006.01)
*C07D 403/10* (2006.01)
*C07D 251/24* (2006.01)
*C09K 11/06* (2006.01)
*C09K 11/02* (2006.01)
*H01L 51/52* (2006.01)

(52) U.S. Cl.
CPC ...... *H01L 51/5004* (2013.01); *H01L 51/5016* (2013.01); *H01L 51/5253* (2013.01); *H01L 2251/5384* (2013.01); *H01L 2251/552* (2013.01)

(56) References Cited

OTHER PUBLICATIONS

European Extended Search Report, European Application No. 15197969.7, dated Apr. 7, 2016, 7 pages.

\* cited by examiner

SPACE-THROUGH CHARGE TRANSFER COMPOUND, AND ORGANIC LIGHT EMITTING DIODE AND DISPLAY DEVICE USING THE SAME

CROSS-REFERENCE TO RELATED APPLICATIONS

This application claims priority to and the benefit of Republic of Korea Patent Application No. 10-2014-0173911 filed on Dec. 5, 2014, and Republic of Korea Patent Application No. 10-2015-0144199 filed on Oct. 15, 2015, all of which are hereby incorporated by reference in their entirety.

BACKGROUND OF THE INVENTION

Field of the Invention

Embodiments of the invention relate to an organic light emitting diode (OLED) and more particularly to a space-through charge transfer compound having excellent emitting efficiency and an OLED and a display device using the space-through charge transfer compound.

Discussion of the Related Art

The requirements of the large-size display device have led to developments in flat panel display devices as an image displaying device. Among the flat panel display devices, the OLED has rapidly developed.

In the OLED, when the electron from a cathode, which serves as an electron-injecting electrode, and the hole from an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption, and color purity.

The OLED includes a first electrode as an anode on a substrate, a second electrode as a cathode facing the first electrode, and an organic emitting layer therebetween.

To improve the emitting efficiency, the organic emitting layer may include a hole injection layer (HIL), a hole transporting layer (HTL), an emitting material layer (EML), an electron transporting layer (HTL), and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such the light is emitted.

The External quantum efficiency of the emitting material for the EML can be expressed by the following equation:

$$\eta_{ext} = \eta_{int} \times \Gamma \times \Phi \times \eta_{out\text{-}coupling}$$

In the above equation, "$\eta_{int}$" is the internal quantum efficiency, "$\Gamma$" is the charge balance factor, "$\Phi$" is the radiative quantum efficiency, and "$\eta_{out\text{-}coupling}$" is the out-coupling efficiency.

The charge balance factor "$\Gamma$" means a balance between the hole and the electron when generating the exciton. Generally, assuming 1:1 matching of the hole and the electron, the charge balance factor has a value of "1". The radiative quantum efficiency "$\Phi$" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of holes and electrons. In the fluorescent compound, a maximum value of the internal quantum efficiency is 0.25. When the hole and the electron are combined to generate the exciton, a ratio of the singlet excitons to the triplet excitons is 1:3 according to the spin structure. However, in the fluorescent compound, only the singlet excitons excluding the triplet excitons are engaged in emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed as 0.2.

Accordingly, the maximum emitting efficiency of the OLED including the fluorescent compound as the emitting material is less than approximately 5%.

To overcome the disadvantage of the emitting efficiency of the fluorescent compound, the phosphorescent compound, where both the singlet excitons and the triplet excitons are engaged in the emission, has been developed for the OLED.

The red and green phosphorescent compounds having a relatively high efficiency are introduced and developed. However, there is no blue phosphorescent compound meeting the requirements in emitting efficiency and reliability.

SUMMARY OF THE INVENTION

Accordingly, the embodiment of the invention is directed to a space-through charge transfer compound and an OLED and a display device using the same that substantially obviate one or more of the problems due to limitations and disadvantages of the related art.

An objective of the embodiment of the invention is to provide a space-through charge transfer compound having high emitting efficiency.

Another objective of the embodiment of the invention is to provide an OLED and a display device having improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, embodiments relate to a space-through charge transfer compound including a paracyclophane core, an electron donor moiety selected from the group consisting of carbazole and diphenyl amine, and an electron acceptor moiety selected from the group consisting of pyrimidine, diphenyltriazine, and triazole, wherein the electron donor moiety and the electron acceptor moiety are indirectly or directly combined to the paracyclophane core with or without a linker, respectively.

Embodiments also relate to a space-through charge transfer compound of

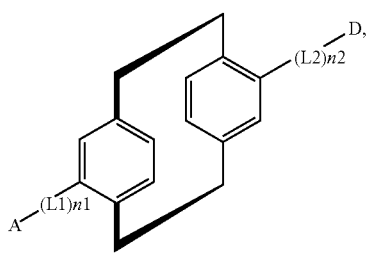

wherein D is selected from

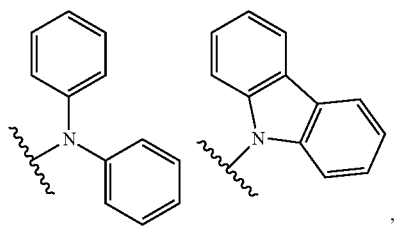

and A is selected from

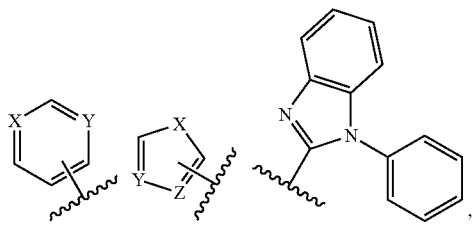

wherein each of L1 and L2 is selected from

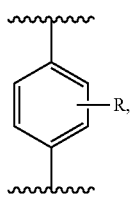

and each of n1 and n2 is 0 (zero) or 1, and wherein R is selected from the group consisting of hydrogen and C1 alkyl to C10 alkyl.

Embodiments also relate to an organic light emitting diode including a first electrode, a second electrode facing the first electrode, and an organic emitting layer between the first and second electrodes and including a space-through charge transfer compound, wherein the space-through charge transfer compound includes a paracyclophane core, an electron donor moiety selected from the group consisting of carbazole and diphenyl amine, and an electron acceptor moiety selected from the group consisting of pyrimidine, diphenyltriazine, and triazole, wherein the electron donor moiety and the electron acceptor moiety are indirectly or directly combined to the paracyclophane core with or without a linker, respectively.

Embodiments also relate to an organic light emitting diode including a first electrode, a second electrode facing the first electrode, and an organic emitting layer between the first and second electrodes and including a space-through charge transfer compound of

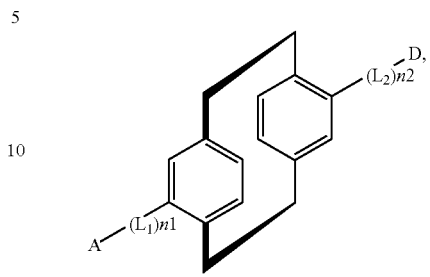

wherein D is selected from

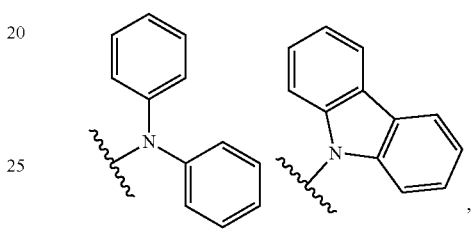

and A is selected from

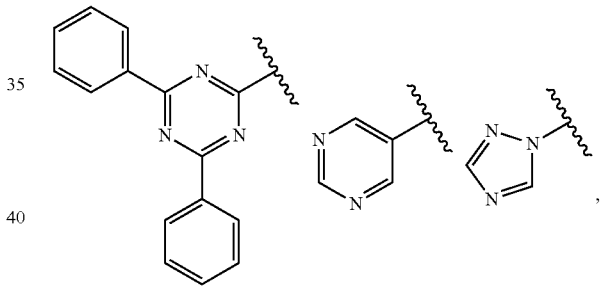

wherein each of L1 and L2 is selected from

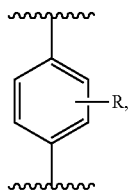

and each of n1 and n2 is 0 (zero) or 1, and wherein R is selected from the group consisting of hydrogen and C1 alkyl to C10 alkyl.

Embodiments also relate to a display device including a substrate, an organic light emitting diode on the substrate and including a first electrode, a second electrode facing the first electrode, and an organic emitting layer between the first and second electrodes and including a space-through charge transfer compound, an encapsulation film on the organic light emitting diode, and a cover window on the encapsulation film, wherein the space-through charge transfer compound includes a paracyclophane core, an electron donor moiety selected from the group consisting of carbazole and diphenyl amine, and an electron acceptor moiety selected from the group consisting of pyrimidine, diphenyltriazine, and triazole, wherein the electron donor moiety and the electron acceptor moiety are indirectly or directly combined to the paracyclophane core with or without a linker, respectively.

Embodiments also relate to a display device including a substrate, an organic light emitting diode on the substrate and including a first electrode, a second electrode facing the first electrode, and an organic emitting layer between the first and second electrodes and including a space-through charge transfer compound of Formula 1, an encapsulation film on the organic light emitting diode, and a cover window on the encapsulation film,

[Formula 1]

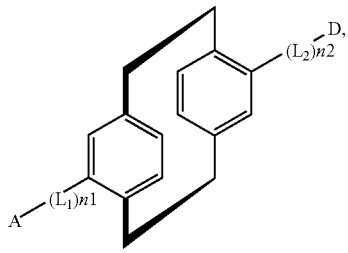

wherein D is selected from

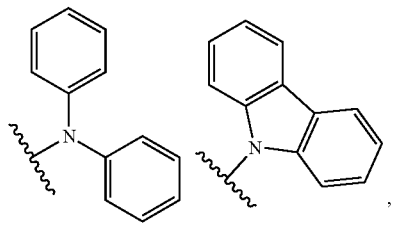

and A is selected from

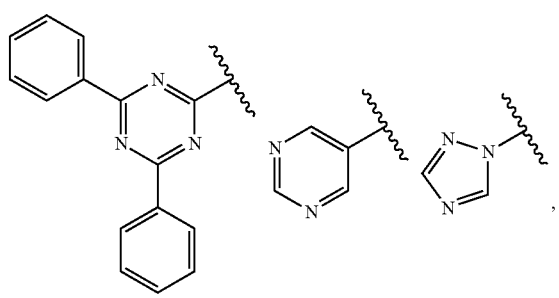

wherein each of L1 and L2 is selected from

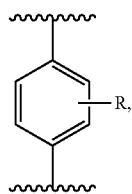

and each of n1 and n2 is 0 (zero) or 1, and wherein R is selected from the group consisting of hydrogen and C1 alkyl to C10 alkyl.

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
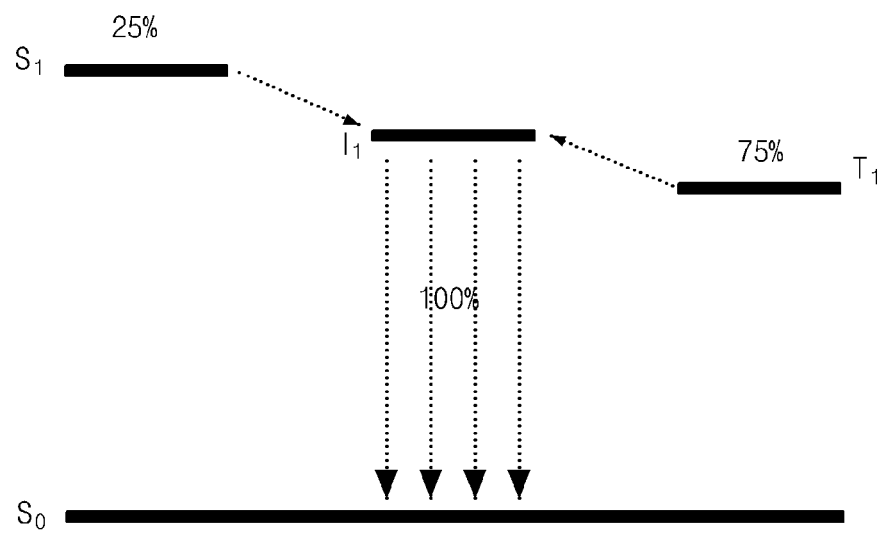
FIG. 1 is a view illustrating an emission mechanism of a space-through charge transfer compound, according to the present invention.

The meanings of terms described in the present specification should be understood as follows.

The singular forms should be understood as including the plural forms as well unless the context clearly indicates otherwise. The terms "first", "second", and the like are used to discriminate any one element from other elements and the scope of the present invention is not intended to be limited by these terms. The terms "comprises" "includes" and the like should be understood as not precluding the presence or addition of one or more other features, integers, steps, operations, elements, components, or combinations thereof. The term "at least one" should be understood as including all combinations that may be suggested from one or more associated items. For example, the meanings of "at least one selected from a first item, a second item, and a third item" includes not only each of the first item, the second item, and the third item, but also all combinations of these items that may be suggested from two or more ones of the first item, the second item, and the third item. In addition, when any one element is referred to as being "on" another element, it can be directly on the upper surface of the other element or a third intervening element may also be present.

Reference will now be made in detail to example embodiments, examples of which are illustrated in the accompanying drawings.

A space-through charge transfer compound of the present invention has a structure in that an electron donor moiety and an electron acceptor moiety are combined or linked to a core of paracyclophane with or without a linker. The space-through charge transfer compound may have Formula 1 of the following.

[Formula 1]

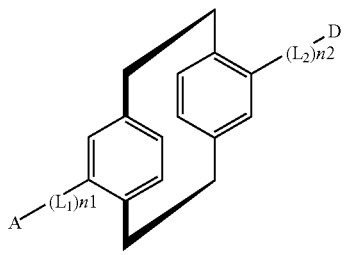

In the Formula 1, each of n1 and n2 is 0 (zero) or 1. Namely, the space-through charge transfer compound in the Formula 1 may have a structure selected from Formulas 2-1 to 2-4 of the following.

[Formula 2-1]

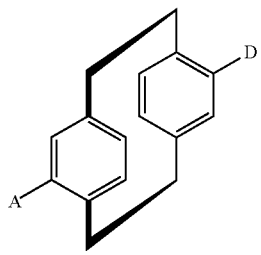

[Formula 2-2]

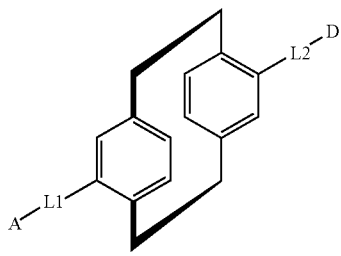

[Formula 2-3]

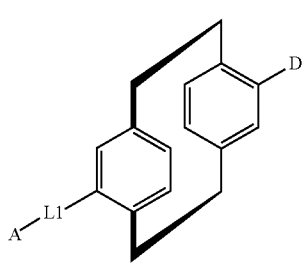

[Formula 2-4]

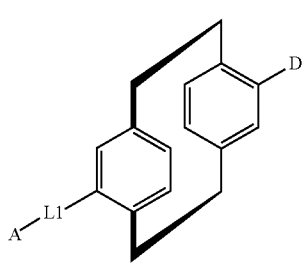

Namely, the space-through charge transfer compound may have a first structure in that the electron donor moiety "D" and the electron acceptor moiety "A" are directly combined or linked to the paracyclophane core as in Formula 2-1 (n1=n2=0), or a second structure in that the electron donor moiety "D" and the electron acceptor moiety "A" are combined or linked to the paracyclophane core with the linkers "L1" and "L2" as in Formula 2-2 (n1=n2=1). Alternatively, the space-through charge transfer compound may have a third structure in that the electron donor moiety "D" is combined to paracyclophane core with the linker "L2" and the electron acceptor moiety "A" is directly combined to the paracyclophane core as in Formula 2-3 (n1=0, n2=1). The space-through charge transfer compound may have a fourth structure in that the electron donor moiety "D" is directly combined to the paracyclophane core and the electron acceptor moiety "A" is combined to the paracyclophane core with the linker "L1" as in Formula 2-4 (n1=1, n2=0).

In Formula 1, the electron donor moiety "D" is selected from the group consisting of carbazole and diphenyl amine. For example, the electron donor moiety "D" may be selected from Formula 3 of the following.

[Formula 3]

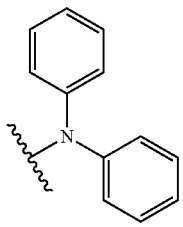 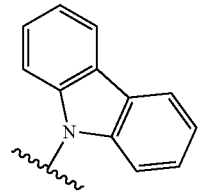

In Formula 1, the electron acceptor moiety "A" is selected from the group consisting of pyrimidine, diphenyltriazine, and triazole. For example, electron acceptor moiety "A" may be selected from Formula 4 of the following.

[Formula 4]

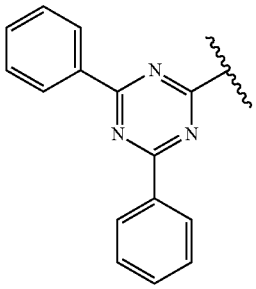 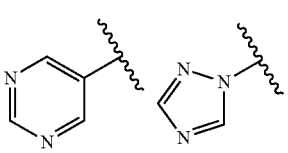 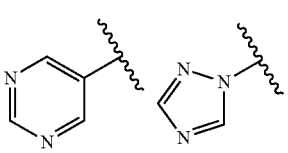

In Formula 1, each of the linkers "L1" and "L2" is independently selected from substituted or non-substituted benzene. For example, each of the linkers "L1" and "L2" may be independently selected from Formula 5 of the following.

[Formula 5]

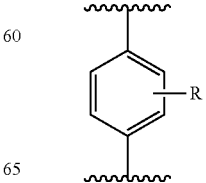

In Formula 5, R is selected from the group consisting of hydrogen and C1 alkyl to C10 alkyl.

In the space-through charge transfer compound, the electron donor moiety and the electron acceptor moiety are combined or linked in the molecule such that an overlap between the highest occupied molecular orbital (HOMO) and the lowest unoccupied molecular orbital (LUMO) is reduced. As a result, a charge transfer complex is generated, and the emitting efficiency of the space-through charge transfer compound is improved. Namely, in the space-through charge transfer compound, the triplet exciton is used for emission such that the emitting efficiency is improved.

In other words, since the space-through charge transfer compound of the present invention includes both of the electron donor moiety and the electron acceptor moiety, the charge is easily transferred in the molecule, and emission efficiency is improved.

In the space-through charge transfer compound of the present invention, since the electron donor moiety and the electron acceptor moiety are combined or linked to the paracyclophane core, a gap or a distance between the electron donor moiety and the electron acceptor moiety is decreased or minimized. Accordingly, the charge transfer is directly generated through a space between the electron donor moiety and the electron acceptor moiety such that the conjugation length in the space-through charge transfer compound becomes shorter than another compound where the charge transfer is generated through a bonding orbital. As a result, a red shift problem in the emitted light can be prevented, and the space-through charge transfer compound of the present invention can provide deep blue emission.

In addition, the space-through charge transfer compound of the present invention includes the benzene linker being capable of minimizing the steric hindrance between the electron donor moiety and the electron acceptor moiety such that the stability of the compound is increased.

Referring to FIG. 1, which is a view illustrating an emission mechanism of a space-through charge transfer compound according to the present invention, in the space-through charge transfer compound of the present invention, the triplet excitons as well as the singlet excitons are engaged in the emission such that the emitting efficiency is improved.

Namely, the triplet exciton is activated by a field, and the triplet exciton and the singlet exciton are transferred into an intermediated state "$I_1$" and transited into a ground state "So" to emit the light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound.

In the related art fluorescence compound, since the HOMO and the LUMO are dispersed throughout an entirety of the molecule, the interconversion of the HOMO and the LUMO is impossible. (Selection Rule.)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety is spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit the light. As a result, the FADF compound has the theoretic quantum efficiency of 100%.

For example, the space-through charge transfer compound in Formula 1 may be one of compounds in Formula 6.

[Formula 6]

compound 1

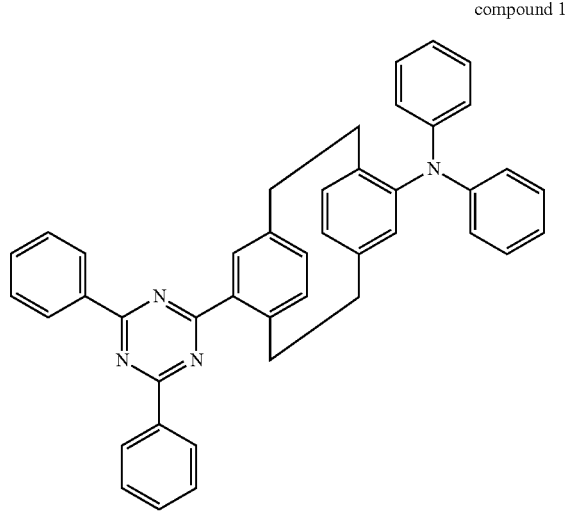

compound 2

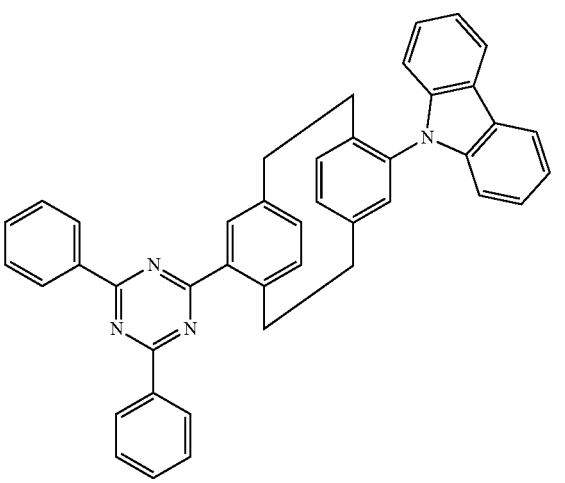

compound 3 compound 4 compound 5 compound 6

The space-through charge transfer compound of the present invention has a wide energy band gap such that the emission efficiency of the OLED using the compound is improved.

Synthesis

1. Synthesis of Compound 1

(1) Compound "a"

[Reaction Formula 1-1]

a

In the $N_2$ gas purging system, 4,16-dibromo[2,2]paracyclophane, diphenylamine (1.1 equivalent), $Pd(OAc)_2$ (0.019 equivalent), $P(t-Bu)_3$ (50 wt %, 0.046 equivalent), and NaOt-Bu (sodium tert-butoxide, 1.9 equivalent) were put into toluene solvent, and the mixture was stirred. The solution was refluxed and stirred for 12 hours under a temperature of 120° C. After completion of the reaction, the solution was cooled into room temperature and was extracted by water and ethylacetate. Moisture was removed from the extracted organic layer by using magnesium sulfate ($MgSO_4$), and the solvent was removed. The resultant was wet-refined by column-chromatography using hexane and ethylacetate such that compound "a" was obtained. (yield: 65%)

(2) Compound "b"

[Reaction Formula 1-2]

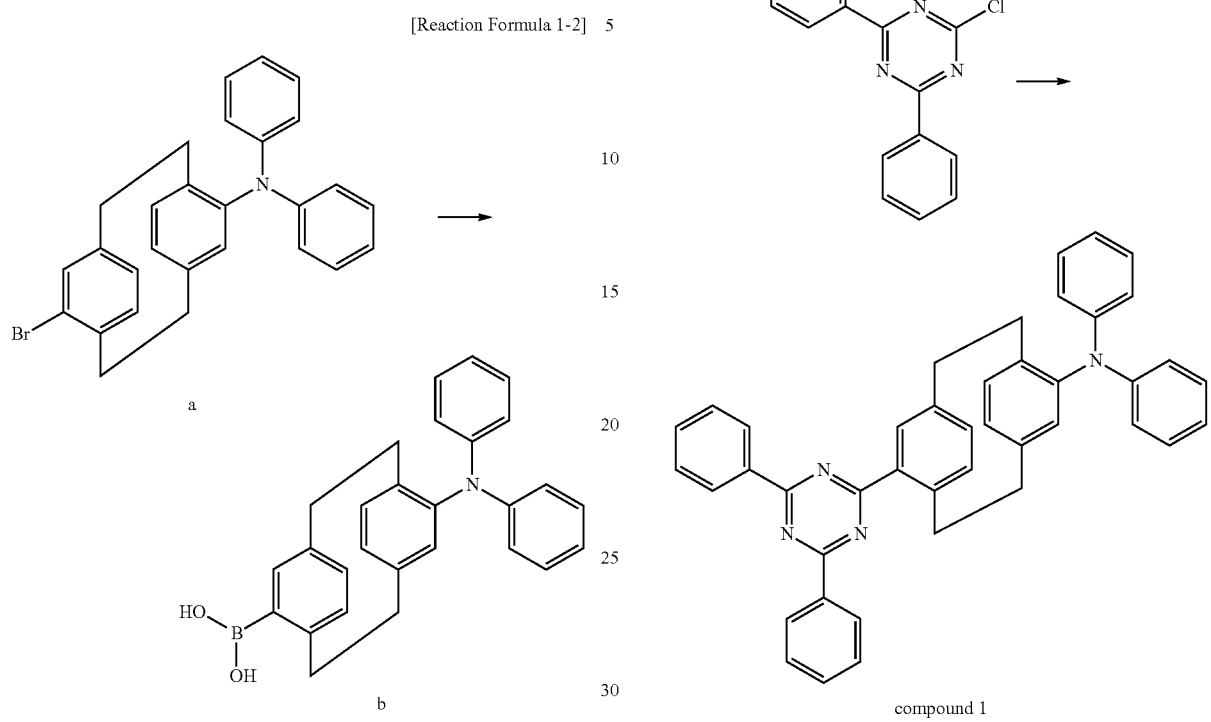

compound 1

In the $N_2$ gas purging system, compound "a" (17.9 mmol) was dissolved in tetrahydrofuran (THF) and was stirred. n-butyl-lithium (26.9 mmol) was slowly added into the solution under a temperature of −78° C., and the mixed solution was stirred for 1 hour. With maintaining the low temperature condition, tri-ethylborate (21.6 mmol) was added, and the mixed solution was stirred under room temperature. The mixed solution was stirred for 12 hours under room temperature, and the reaction was completed. Distilled water was slowly added, and mixed solution of distilled water/hydrochloric acid (HCl) (8:2) was added to be pH2. The solution was extracted using distilled water and ethylacetate. Moisture was removed from the extracted organic layer by using magnesium sulfate, and the solvent was removed. The resultant was wet-refined by column-chromatography using hexane and ethylacetate such that compound "b" was obtained. (yield: 80%)

(3) Compound 1

[Reaction Formula 1-3]

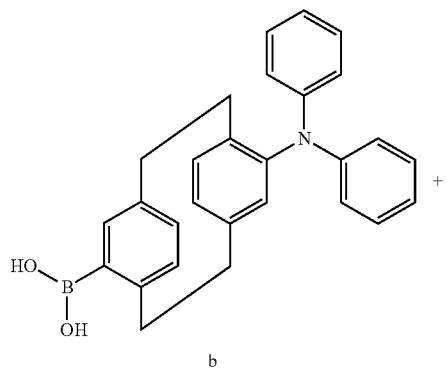

In the $N_2$ gas purging system, 2-chloro-4,6-diphenyl-1,3,5-triazine, compound "b" (1 equivalent), sodium carbonate ($Na_2CO_3$, 0.6 equivalent) were put into solvent of toluene/dioxane/distilled water (1:1:0.7) and stirred. $Pd(PPh_3)_4$ (tetrakis(triphenylphosphine)palladium(0), 0.3 equivalent) was additionally added and stirred for 16 hours. After completion of the reaction, the solution was cooled into room temperature. The organic layer was washed and filtered by distilled water in silica-gel. The solvent and distilled water were removed, and the resultant was re-crystallized by chloroform and dried such that compound "1" was obtained. (yield: 75%)

2. Synthesis of Compound 2

(1) Compound "c"

[Reaction Formula 2-1]

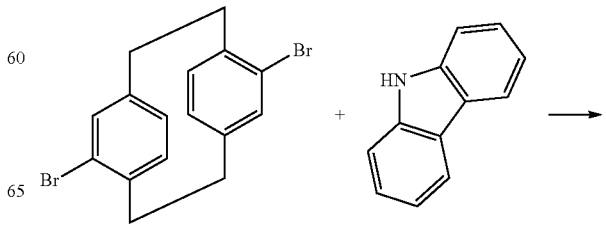

-continued

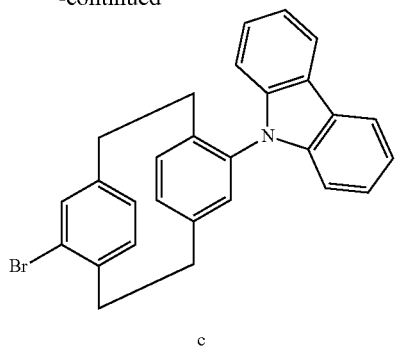

c

In the N₂ gas purging system, carbazole was dissolved 1,4-dioxane solvent, and CuI and K₃PO₄ were added. 4,16-dibromo[2,2]paracyclophane (1.1 equivalent) and trans-1,2-diaminocyclohexane were additionally added. The solution was refluxed and stirred for 24 hours under a temperature of 110° C. After completion of the reaction, the solution was cooled into room temperature and extracted by ethylacetate and distilled water. Moisture was removed from the extracted organic layer by using magnesium sulfate, and remaining organic solvent was removed. The resultant was wet-refined by column-chromatography using ethylacetate and hexane such that compound "c" was obtained. (yield: 63%)

(2) Compound 2

[Reaction Formula 1-2]

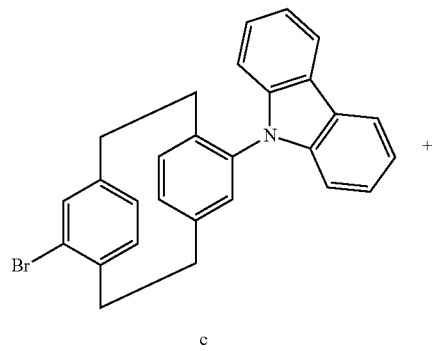

c

+

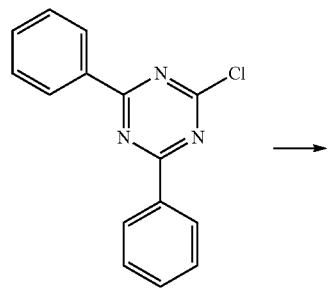

-continued

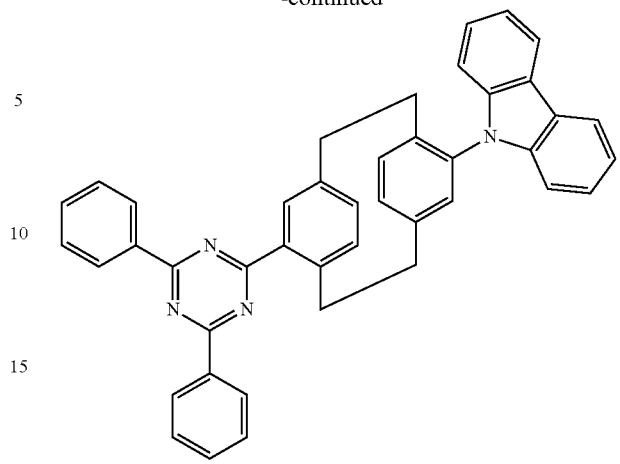

compound 2

In the N₂ gas purging system, 2-chloro-4,6-diphenyl-1,3,5-triazine, compound "c" (1 equivalent), sodium carbonate (Na₂CO₃, 0.6 equivalent) were put into solvent of toluene/dioxane/distilled water (1:1:0.7) and stirred. Pd(PPh₃)₄ (tetrakis(triphenylphosphine)palladium(0), 0.3 equivalent) was additionally added and stirred for 16 hours. After completion of the reaction, the solution was cooled into room temperature. The organic layer was washed and filtered by distilled water in silica-gel. The solvent and distilled water were removed, and the resultant was re-crystallized by chloroform and dried such that compound "2" was obtained. (yield: 70%)

3. Synthesis of Compound 3

[Reaction Formula 3]

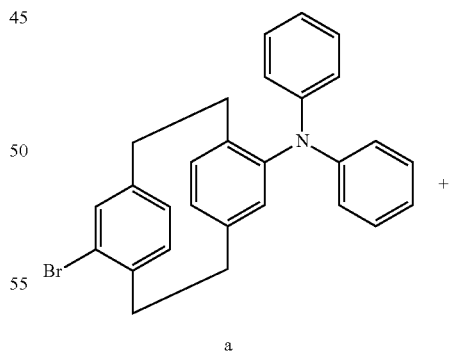

a

+

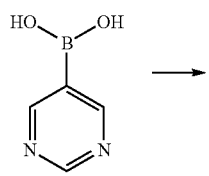

17
-continued

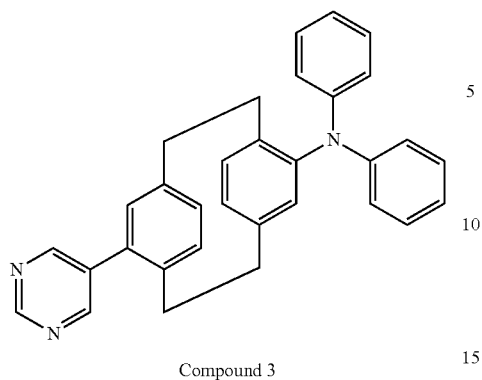

Compound 3

In the N$_2$ gas purging system, the reactant of compound "a", 5-pyrimidylboronic acid (1.5 equivalent), Pd(dppf)Cl$_2$ (4 mol %), and K$_3$PO$_4$ (2 equivalent) were put into toluene solvent and stirred. The solution was refluxed and stirred for 24 hours. After completion of the reaction, the solution was cooled into room temperature and was diluted by adding toluene. The solution was hydrolyzed by 10% NaOH and was extracted by ethylacetate. Moisture was removed from the extracted organic layer by using magnesium sulfate, and remaining organic solvent was removed. The resultant was wet-refined by column-chromatography using ethylacetate and hexane such that compound 3 was obtained. (yield: 80%)

4. Synthesis of Compound 4

[Reaction Formula 4]

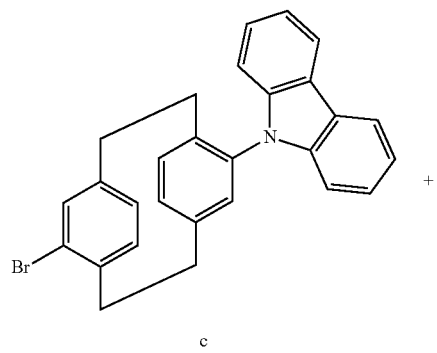

c

+

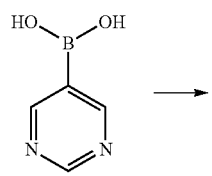

18
-continued

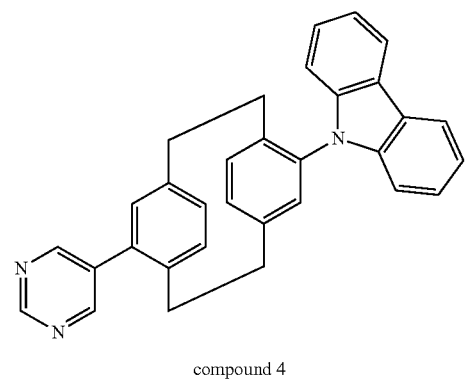

compound 4

In the N$_2$ gas purging system, the reactant of compound "c", 5-pyrimidylboronic acid (1.5 equivalent), Pd(dppf)Cl$_2$ (4 mol %), and K$_3$PO$_4$ (2 equivalent) were put into toluene solvent and stirred. The solution was refluxed and stirred for 24 hours. After completion of the reaction, the solution was cooled into room temperature and was diluted by adding toluene. The solution was hydrolyzed by 10% NaOH and was extracted by ethylacetate. Moisture was removed from the extracted organic layer by using magnesium sulfate, and remaining organic solvent was removed. The resultant was wet-refined by column-chromatography using ethylacetate and hexane such that compound 4 was obtained. (yield: 70%)

5. Synthesis of Compound 5

[Reaction Formula 5]

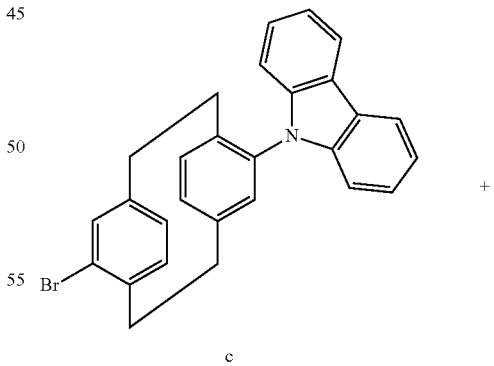

c

+

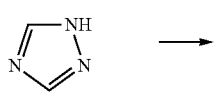

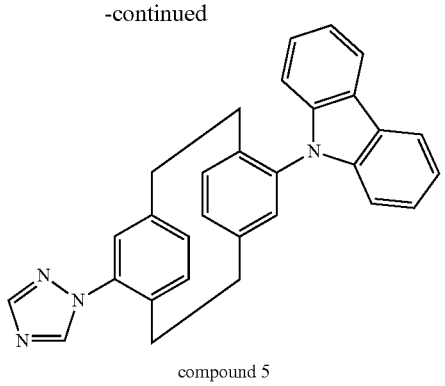

compound 5

In the N₂ gas purging system, 1,2,4-triazole (1.5 equivalent), compound "c", K₂CO₃ (2 equivalent), and copper(I) 3-methylsalicylate (0.01 equivalent) were put into dimethyl sulfoxide (DMSO) solvent and stirred. The solution was stirred for 3 hours under a temperature of 110° C. and was cooled into room temperature. The solution was filtered and washed by using small quantity dimethyl sulfoxide (DMSO). The solution was extracted by cold distilled water and ethylacetate. Moisture was removed from the extracted organic layer by using magnesium sulfate, and remaining organic solvent was removed. The resultant was wet-refined by column-chromatography using ethylacetate and hexane and re-crystallized such that compound 5 was obtained. (yield: 50%)

6. Synthesis of Compound 6

(1) Compound "d"

[Reaction Formula 6-1]

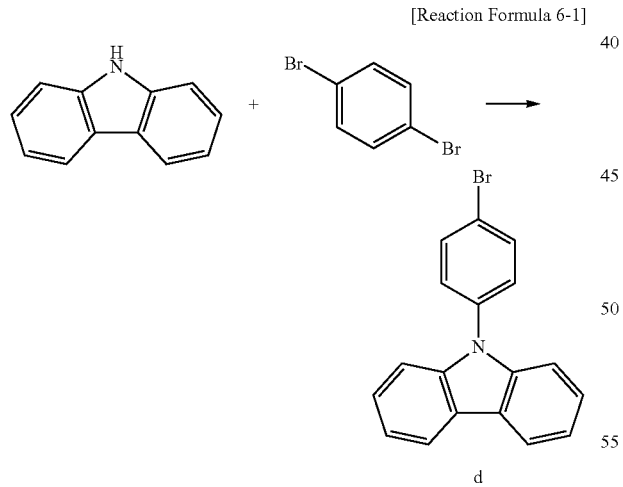

d

In the N₂ gas purging system, carbazole (29.9 mmol), 1,4-dibroobenzene (44.9 mmol), paradium(II)acetate (2 mol %), tri-tert-butylphosphate (5 mol %), and sodium-tert-butoxide (2.03 equivalent) were put into toluene solvent and stirred. The solution was refluxed and stirred to react for 12 hours. After completion of the reaction, the solution was extracted b distilled water and ethylacetate. Moisture was removed from the extracted organic layer by using magnesium sulfate (MgSO₄), and the solvent was removed. The resultant was wet-refined by column-chromatography using ethylacetate and hexane such that compound "d" was obtained. (yield: 80%)

(2) Compound "e"

[Reaction Formula 6-2]

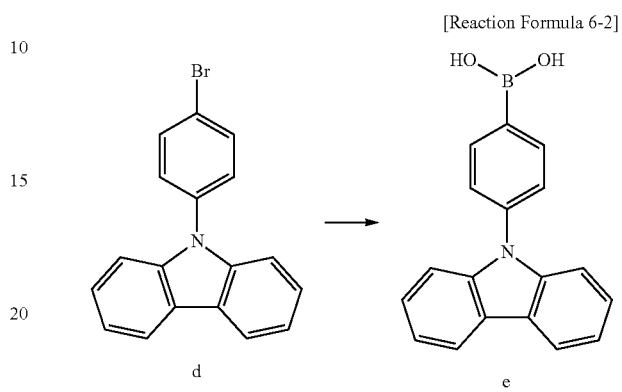

d → e

In the N₂ gas purging system, compound "d" (17.9 mmol) was dissolved in THF solvent and was stirred. n-butyl-lithium (26.9 mmol) was slowly added into the solution under a temperature of −78° C., and the mixed solution was stirred for 1 hour. With maintaining the low temperature condition, tri-ethylborate (21.6 mmol) was added, and the mixed solution was stirred under room temperature. The mixed solution was stirred for 12 hours under room temperature, and the reaction was completed. Distilled water was slowly added, and a mixed solution of distilled water/hydrochloric acid (HCl) (8:2) was added to be pH2. The solution was extracted using distilled water and ethylacetate. Moisture was removed from the extracted organic layer by using magnesium sulfate, and the solvent was removed. The resultant was wet-refined by column-chromatography using hexane and ethylacetate such that compound "e" was obtained. (yield: 87%)

(3) Compound "f"

[Reaction Formula 6-3]

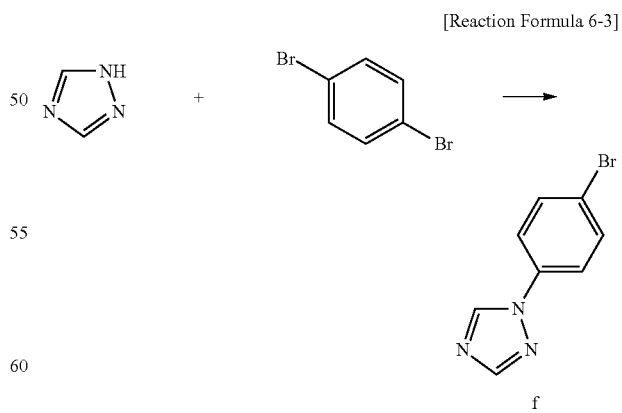

f

In the N₂ gas purging system, 1,2,4-triazole (1 equivalent), 1,4-dibromobenzene, K₂CO₃ (2 equivalent), and copper(I)3-methylsalicylate (0.01 equivalent) were put into dimethyl sulfoxide (DMSO) solvent and stirred. The solution was stirred for 3 hours under a temperature of 110° C. and was cooled into room temperature. The solution was filtered and washed by using small quantity DMSO. The solution was extracted by cold distilled water and ethylacetate. Moisture was removed from the extracted organic layer by using magnesium sulfate, and remaining organic solvent was removed. The resultant was wet-refined by column-chromatography using ethylacetate and hexane and re-crystallized such that compound "f" was obtained. (yield: 56%)

(4) Compound "g"

[Reaction Formula 6-4]

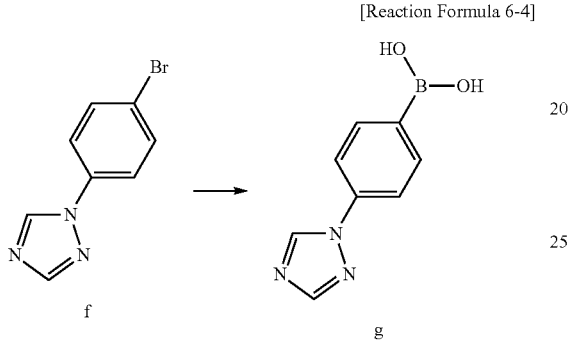

f
g

In the $N_2$ gas purging system, compound "f" was dissolved in THF solvent and was stirred. n-butyl-lithium (1.5 equivalent) was slowly added into the solution under a temperature of −78° C., and the mixed solution was stirred for 1 hour. With maintaining the low temperature condition, tri-ethylborate (1.2 equivalent) was added, and the mixed solution was stirred under room temperature. The mixed solution was stirred for 12 hours under room temperature, and the reaction was completed. Distilled water was slowly added, and a mixed solution of distilled water/hydrochloric acid (HCl) (8:2) was added to be pH2. The solution was extracted using distilled water and ethylacetate. Moisture was removed from the extracted organic layer by using magnesium sulfate, and the solvent was removed. The resultant was wet-refined by column-chromatography using hexane and ethylacetate such that compound "g" was obtained. (yield: 79%)

(5) Compound "h"

[Reaction Formula 6-5]

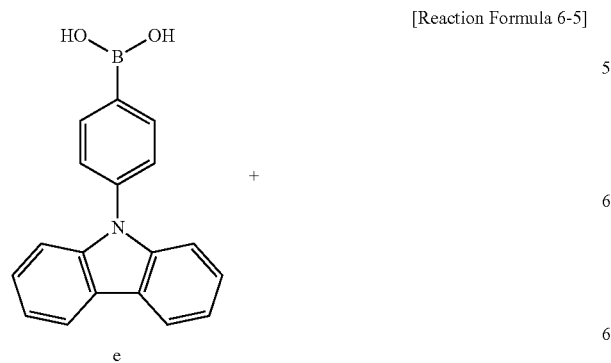

e

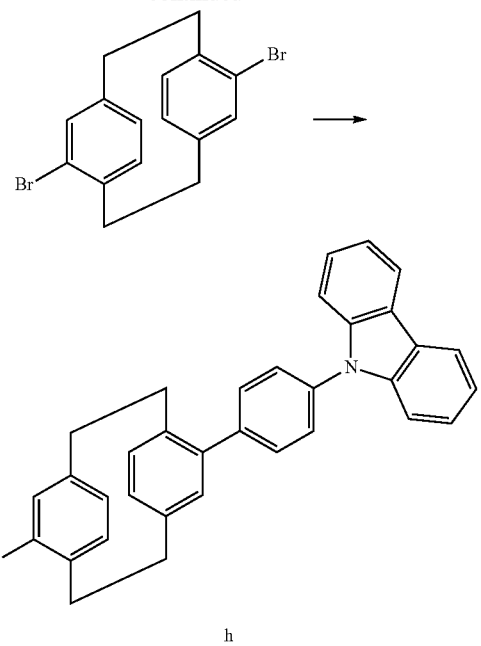

h

In the $N_2$ gas purging system, the reactant of 4,16-dibromo[2,2]paracyclophane, compound "e" (1.1 equivalent), Pd(dppf)Cl$_2$ (4 mol %), and K$_3$PO$_4$ (2 equivalent) were put into toluene solvent and stirred. The solution was refluxed and stirred for 24 hours. After completion of the reaction, the solution was cooled into room temperature and was diluted by adding toluene. The solution was hydrolyzed by 10% NaOH and was extracted by ethylacetate. Moisture was removed from the extracted organic layer by using magnesium sulfate, and remaining organic solvent was removed. The resultant was wet-refined by column-chromatography using ethylacetate and hexane such that compound "h" was obtained. (yield: 80%)

(6) Compound 6

[Reaction Formula 6-6]

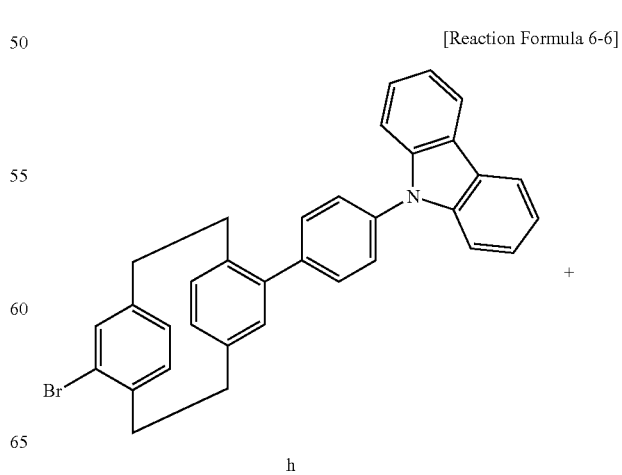

h

-continued

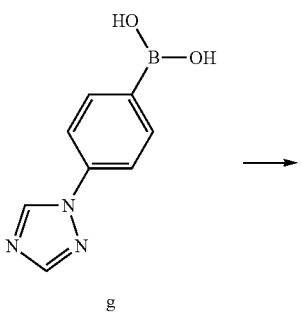

g

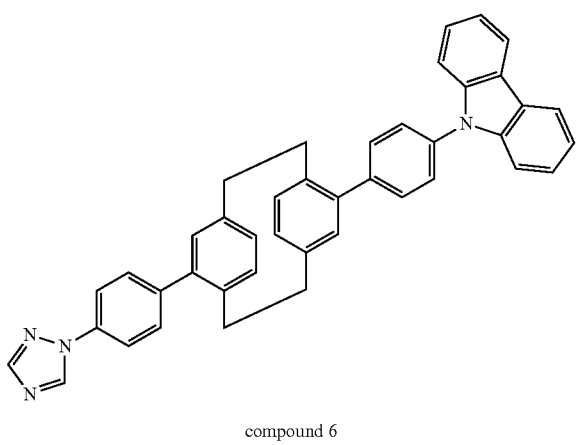

compound 6

In the $N_2$ gas purging system, the reactant of compound "h", compound "g" (1.3 equivalent), $Pd(dppf)Cl_2$ (4 mol %), and $K_3PO_4$ (2 equivalent) were put into toluene solvent and stirred. The solution was refluxed and stirred for 24 hours. After completion of the reaction, the solution was cooled into room temperature and was diluted by adding toluene. The solution was hydrolyzed by 10% NaOH and was extracted by ethylacetate. Moisture was removed from the extracted organic layer by using magnesium sulfate, and remaining organic solvent was removed. The resultant was wet-refined by column-chromatography using ethylacetate and hexane such that compound 6 was obtained. (yield: 58%)

The mass spectrum data of the above compounds 1 to 6 are listed in Table 1.

TABLE 1

|      |           | Calculation | Found (M(H+)) |
|------|-----------|-------------|---------------|
| Com1 | C43H34N4  | 606.28      | 606.28        |
| Com2 | C43H32N4  | 604.26      | 604.26        |
| Com3 | C32H27N3  | 453.22      | 453.22        |
| Com4 | C32H25N3  | 451.2       | 451.2         |
| Com5 | C30H24N4  | 440.2       | 440.2         |
| Com6 | C42H32N4  | 592.26      | 592.26        |

Figure 2A:
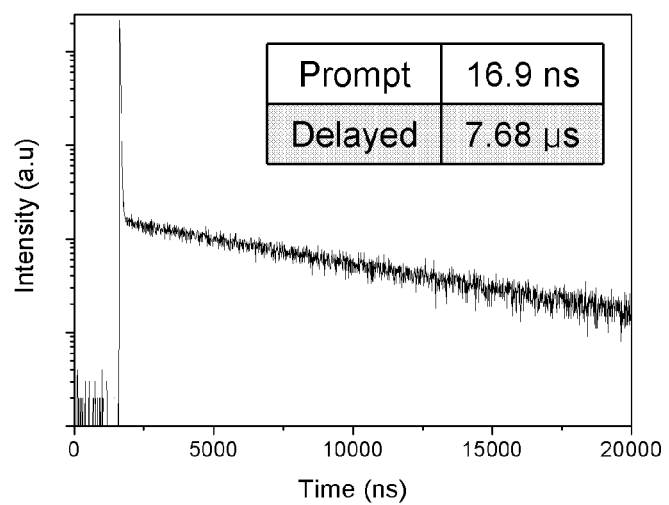
FIGS. 2A to 2C are graphs showing a delayed fluorescent property of a space-through charge transfer compound, according to the present invention.
Figure 2B:
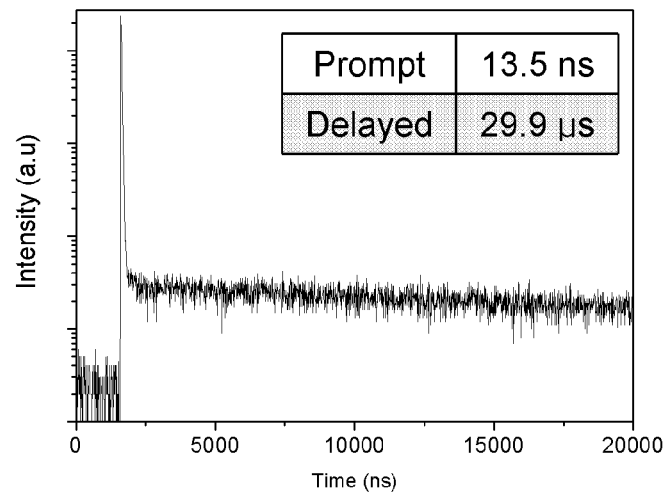
Figure 2C:
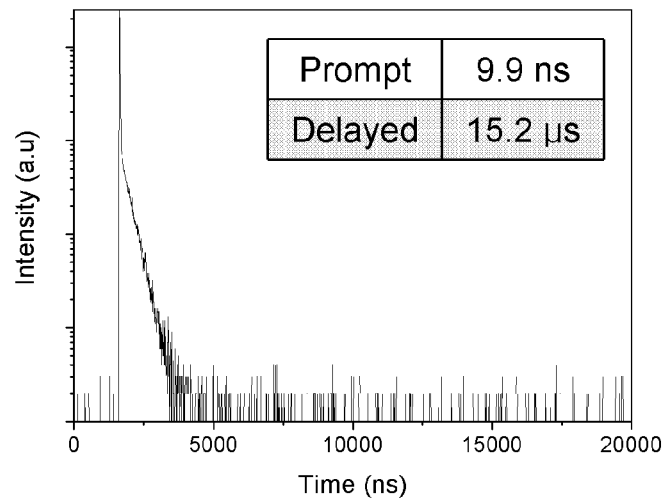

The emission properties of the above compounds 1, 3, and 5 (Com1, Com3, and Com5) are measured and the results are listed in Table 2 and shown in FIGS. 2A to 2C. (Quantarus tau apparatus of Hamamatsu Co., Ltd. $O_2$ free condition.)

TABLE 2

| Fluorescence (ns) | Delayed fluorescence (ns) |
|-------------------|---------------------------|
| 16.9              | 7680                      |

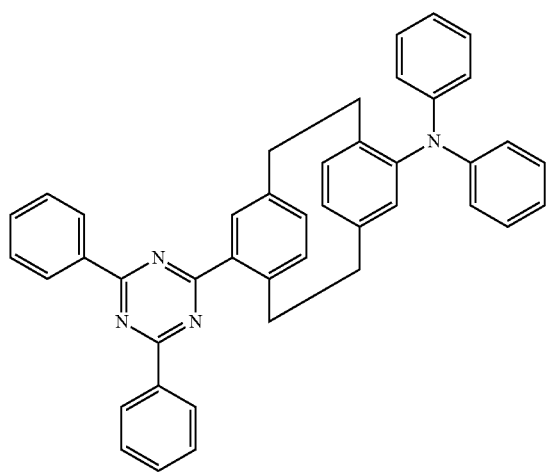

Com1

TABLE 2-continued

| | Fluorescence (ns) | Delayed fluorescence (ns) |
|---|---|---|
| 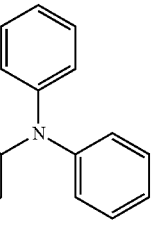<br>Com3 | 13.5 | 29900 |
| 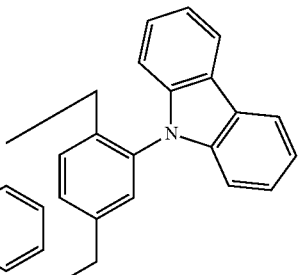<br>Com5 | 9.9 | 15200 |

As shown in Table 2 and FIGS. 2A and 2C, the space-through charge transfer compounds (Com1, Com3 and Com5) of the present invention show the delayed fluorescent emission (Delayed) of thousands to tens of thousands nanoseconds (ns) with the fluorescent emission (Prompt).

As mentioned above, the space-through charge transfer compound of the present invention is activated by the field such that the excitons in the singlet state "$S_1$" and the triplet state "$T_1$" are transited into the intermediated state "$I_1$". As a result, both the excitons in the singlet state "$S_1$" and the excitons in the triplet state "$T_1$" are engaged in emission.

The FADF compound is a single molecule compound having the electron donor moiety and the electron acceptor moiety in the single molecule such that the charge transfer is easily generated through a space in the molecule. In the FADF compound with particular conditions, the charge can be separated from the electron donor moiety to the electron acceptor moiety through the space between the electron donor moiety to the electron acceptor moiety.

The FADF compound is activated by outer factors. It can be verified by comparing the absorption peak and the emission peak of the solution of the compounds.

$$\Delta v = vabs - vfl = \frac{2\Delta\mu^2}{hca^3}\Delta f + \text{constant} \quad \text{(Lippert} - \text{Mataga equation)}$$

In the above equation, "$\Delta v$" is the Stock-shift value, and "υabs" and "υfl" are the wave-number of the maximum absorption peak and the maximum emission peak, respectively. "h" is Planck's constant, "c" is the velocity of light, "a" is the onsager cavity radius, and "$\Delta\mu$" is a difference between the dipole moment of the excited state and the dipole moment of the ground state. ($\Delta\mu=\mu_e-\mu_g$)

"$\Delta f$" is a value indicating the orientational polarizability of the solvent and may be a function of the dielectric constant of the solvent (ε) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the FADF can be verified by comparing the absorption peak and the emission peak of the solution of the compounds.

The orientational polarizability ($\Delta f$) of the mixed solvent can be calculated by using the orientational polarizability of each pure solvent and their mole fraction. When "$\Delta f$" and "$\Delta v$" are linearly plotted by using above "Lippert-Mataga equation", the compound may provide the FADF emission.

Namely, when the FADF complex is stabilized according to the orientational polarizability of the solvent, the emission peak is shifted in a long wavelength according to the degree of the stabilization. Accordingly, when the compound provides the FADF emission, "$\Delta f$" and "$\Delta v$" are plotted in a linear line. When "$\Delta f$" and "$\Delta v$" are plotted in a linear line, the compound provides the FADF emission.

In the space-through charge transfer compound of the present invention, the 25% excitons in the singlet state and the 75% excitons in the triplet state are transited into the intermediate state by an outer force, i.e., a field generated when the OLED is driven. (Intersystem crossing.) The excitons in the intermediate state are transited into the ground state such that the emitting efficiency is improved. Namely, in the fluorescent compound, since the singlet exciton and the triplet exciton are engaged in emission, the emitting efficiency is improved.

OLED

An ITO layer is deposited on a substrate and washed to form an anode (3 mm*3 mm). The substrate is loaded in a vacuum chamber, and a hole injecting layer (500 Å, NPB (N,N'-di(naphthalen-1-yl)-N,N'-diphenyl-benzidine)), a hole transporting layer (100 Å, mCP(N,N'-Dicarbazolyl-3,5-benzene)), an emitting material layer (300 Å, host (bis{2-[di(phenyl)phosphino]phenyl}ether oxide) and dopant (6%)), an electron transporting layer (300 Å, 1,3,5-tri(phenyl-2-benzimidazole)-benzene), an electron injecting layer (LiF), and a cathode (Al) are sequentially formed on the anode under a base pressure of about $10^{-6}$ to $10^{-7}$ Torr.

(7) Comparative Example (Ref)

The reference compound in Formula 7 of the following is used as the dopant to form the OLED.

(2) Example 1 (Ex1)

The compound 1 is used as the dopant to form the OLED.

(3) Example 2 (Ex2)

The compound 3 is used as the dopant to form the OLED.

(4) Example 3 (Ex3)

The compound 5 is used as the dopant to form the OLED.

[Formula 7]

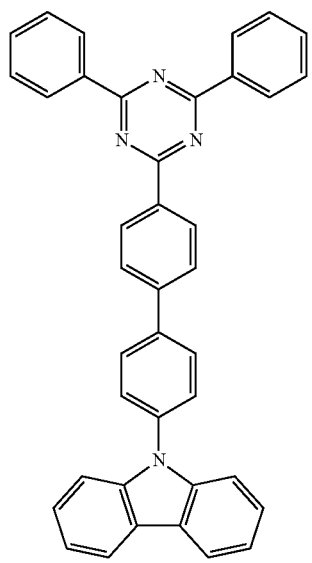

TABLE 3

| | Voltage (V) | Cd/A | lm/W | EQE (%) | CIE (X) | CIE (Y) |
| --- | --- | --- | --- | --- | --- | --- |
| Ref | 7.75 | 6.82 | 2.76 | 4.00 | 0.171 | 0.269 |
| Ex1 | 5.53 | 17.39 | 9.88 | 9.78 | 0.169 | 0.2898 |
| Ex2 | 5.48 | 8.87 | 5.08 | 5.66 | 0.170 | 0.235 |
| Ex3 | 6.32 | 12.80 | 6.36 | 7.19 | 0.173 | 0.288 |

As shown in Table 3, the OLEDs using the compounds of the present invention (Ex1 to Ex3) have advantages in the driving voltage, the emitting efficiency, and so on.

Figure 3:
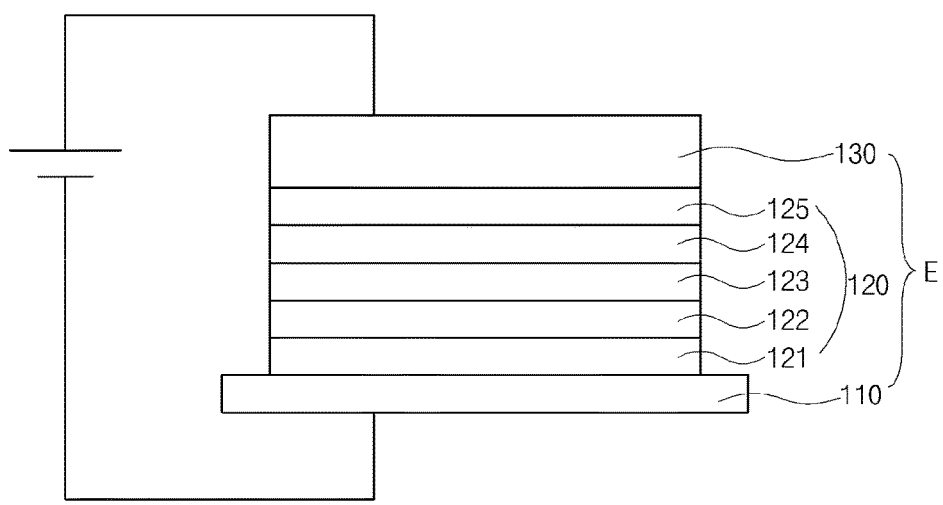
FIG. 3 is a schematic cross-sectional view of an organic light emitting diode (OLED) according to the invention.

FIG. 3 is a schematic cross-sectional view of an OLED according to the invention.

As shown in FIG. 3, the OLED "E" is formed on a substrate (not shown). The OLED "E" includes a first electrode 110 as an anode, a second electrode 130 as a cathode, and an organic emitting layer 120 therebetween.

Although not shown, an encapsulation film, which includes at least one inorganic layer and at least one organic layer and covers the OLED "E", and a cover window on the encapsulation film may be further formed to form a display device including the OLED "E". The substrate, the encapsulation film, and the cover window may have a flexible property such that a flexible display device may be provided.

The first electrode 110 is formed of a material having a relatively high work function, and the second electrode 130 is formed of a material having a relatively low work function. For example, the first electrode 110 may be formed of indium-tin-oxide (ITO), and the second electrode 130 may be formed of aluminum (Al) or Al alloy (AlNd). The organic emitting layer 120 may include red, green, and blue emitting patterns.

The organic emitting layer 120 may have a single-layered structure. Alternatively, to improve the emitting efficiency, the organic emitting layer 120 includes a hole injection layer (HIL) 121, a hole transporting layer (HTL) 122, an emitting material layer (EML) 123, an electron transporting layer (ETL) 124, and an electron injection layer (EIL) 125 sequentially stacked on the first electrode 110.

At least one selected from the HIL 121, the HTL 122, the EML 123, the ETL 124, and the EIL 125 includes the space-through charge transfer compound in Formula 1.

For example, the EML 123 may include the space-through charge transfer compound in Formula 1. The space-through charge transfer compound acts as the dopant, and the EML 123 may further include a host to emit the blue light. In this instance, the dopant has about 1 to 30 weight % with respect to the host.

A difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV. ($|HOMO_{Host}-HOMO_{Dopant}|\leq 0.5$ eV or $|LUMO_{Host}-LUMO_{Dopant}|\leq 0.5$ eV) In this instance, the charge transfer efficiency from the host to the dopant may be improved.

The triplet energy of the dopant is smaller than the triplet energy of the host, and a difference between the singlet energy of the dopant and the triplet energy of the dopant is less than 0.3 eV. ($\Delta E_{ST}$ 0.3 eV) As the difference "$\Delta E_{ST}$" is smaller, the emitting efficiency is higher. In the space-through charge transfer compound of the present invention, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

For example, the host, which meets the above condition, may be selected from materials in Formula 8. (Bis[2-(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSO1), 9-(9-phenyl-9H-carbazol-6-yl)-9H-carbazole (CCP) in order.)

[Formula 8]

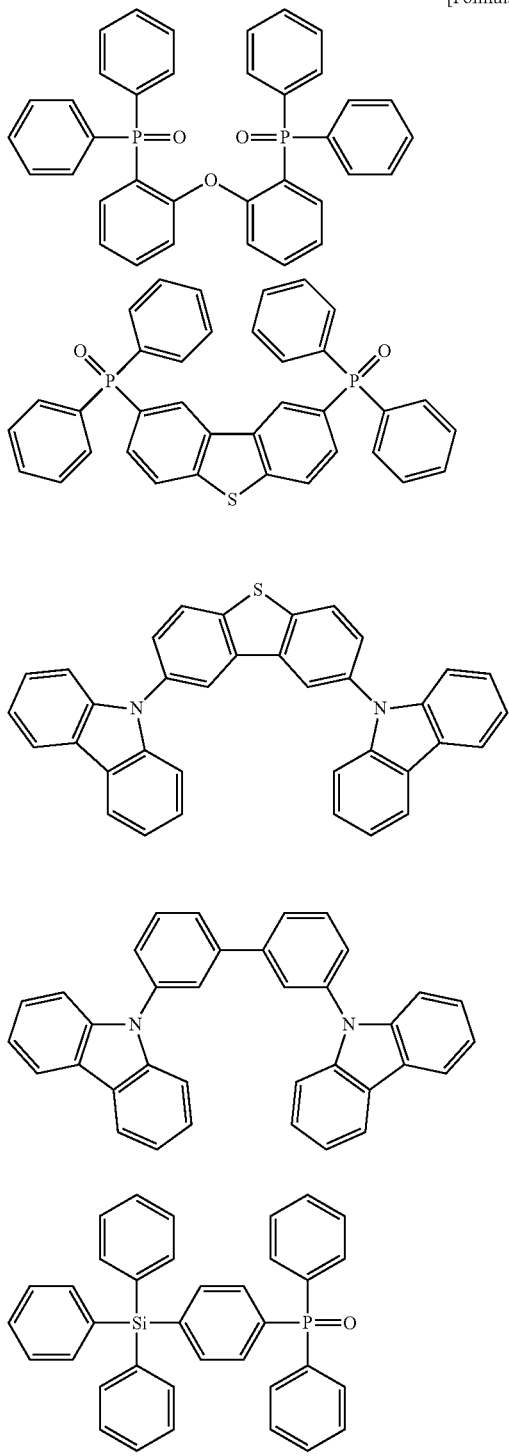

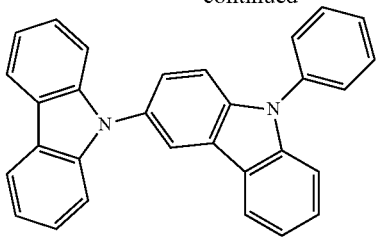

On the other hand, the space-through charge transfer compound of the present invention may act as a host in the EML 123, and the EML 123 may further include a dopant to emit the blue light. In this instance, the dopant has about 1 to 30 weight % with respect to the host. Since the development of the blue host having excellent properties is insufficient, the space-through charge transfer compound of the present invention may be used as the host to increase the degree of freedom for the host. In this instance, the triplet energy of the dopant may be smaller than the triplet energy of the host of the space-through charge transfer compound of the present invention.

The EML 123 may include a first dopant of the space-through charge transfer compound of the present invention, a host, and a second dopant. The weight % summation of the first and second dopants may be about 1 to 30 to emit the blue light. In this instance, the emitting efficiency and the color purity may be further improved.

In this instance, the triplet energy of the first dopant, i.e., the space-through charge transfer compound of the present invention, may be smaller than the triplet energy of the host and larger than the triplet energy of the second dopant. In addition, a difference between the singlet energy of the first dopant and the triplet energy of the first dopant is less than 0.3 eV. ($\Delta E_{ST}$ 0.3 eV) As the difference "$\Delta E_{ST}$" is smaller, the emitting efficiency is higher. In the space-through charge transfer compound of the present invention, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

As mentioned above, in the space-through charge transfer compound of the present invention, since the electron donor moiety and the electron acceptor moiety are combined or linked in one molecule and the overlap between the HOMO and the LUMO is decreased, the space-through charge transfer compound of the present invention acts as a charge transfer complex such that the emitting efficiency of the compound is improved. Namely, in the space-through charge transfer compound of the present invention, the excitons in the triplet state are engaged in the emission such that the emitting efficiency of the compound is improved.

In addition, since the electron donor moiety and the electron acceptor moiety are combined or linked to the paracyclophane core, a space between the electron donor moiety and the electron acceptor moiety is decreased or minimized. Accordingly, the charge transfer is directly generated through the space between the electron donor moiety and the electron acceptor moiety such that the conjugation length is decreased. As a result, the red shift problem in the emitted light is prevented. Namely, the OLED using the space-through charge transfer compound of the present invention can emit the deep blue light. Accordingly, the OLED using the space-through charge transfer compound of the present invention has advantages in the emitting efficiency and image quality.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. A space-through charge transfer compound of Formula 1:

[Formula 1]

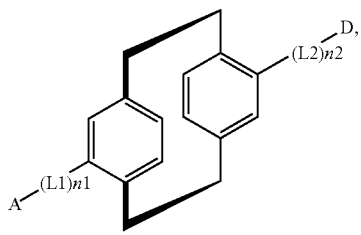

wherein D is selected from Formula 2, and A is selected from Formula 3, wherein each of L1 and L2 is substituted or non-substituted benzene, and each of n1 and n2 is 0 (zero) or 1:

[Formula 2]

[Formula 3]

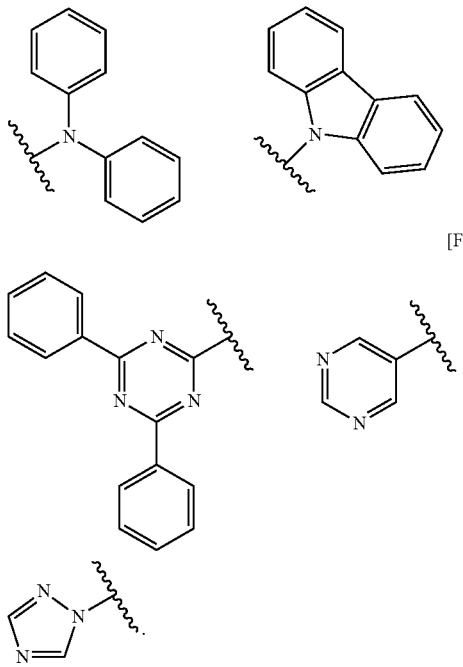

2. The space-through charge transfer compound according to claim 1, wherein a difference between a singlet energy of the space-through charge transfer compound and a triplet energy of the space-through charge transfer compound is less than 0.3 eV.

3. An organic light emitting diode, comprising:
a first electrode;
a second electrode facing the first electrode; and
an organic emitting layer between the first electrode and the second electrode, the organic emitting layer including a space-through charge transfer compound,
wherein the space-through charge transfer compound includes a paracyclophane core, an electron donor moiety selected from the group consisting of carbazole and diphenyl amine, and an electron acceptor moiety selected from the group consisting of pyrimidine, diphenyltriazine, and triazole,
wherein the electron donor moiety and the electron acceptor moiety are indirectly or directly combined to the paracyclophane core with or without a linker, respectively, and
wherein the organic emitting layer further includes a host, and the space-through charge transfer compound is used as a dopant.

4. The organic light emitting diode according to claim 3, wherein the organic emitting layer includes a hole injection layer (HIL), a hole transporting layer (HTL), an emitting material layer (EML), an electron transporting layer (ETL), and an electron injection layer (EIL), and
wherein at least one of the HIL, the HTL, the EML, the ETL, and the EIL includes the space-through charge transfer compound.

5. The organic light emitting diode according to claim 3, wherein a difference between a singlet energy of the space-through charge transfer compound and a triplet energy of the space-through charge transfer compound is less than 0.3 eV.

6. The organic light emitting diode according to claim 3, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

7. An organic light emitting diode, comprising:
a first electrode;
a second electrode facing the first electrode; and
an organic emitting layer between the first electrode and the second electrode, the organic emitting layer including a space-through charge transfer compound,
wherein the space-through charge transfer compound includes a paracyclophane core, an electron donor moiety selected from the group consisting of carbazole and diphenyl amine, and an electron acceptor moiety selected from the group consisting of pyrimidine, diphenyltriazine, and triazole,
wherein the electron donor moiety and the electron acceptor moiety are indirectly or directly combined to the paracyclophane core with or without a linker, respectively,
wherein the organic emitting layer further includes a host and a first dopant, and the space-through charge transfer compound is used as a second dopant, and
wherein a triplet energy of the second dopant is smaller than a triplet energy of the host and larger than a triplet energy of the first dopant.

8. An organic light emitting diode, comprising:
a first electrode;
a second electrode facing the first electrode; and
an organic emitting layer between the first electrode and the second electrode, the organic emitting layer including a space-through charge transfer compound of Formula 1:

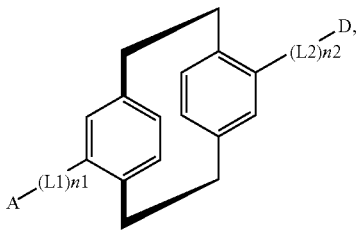

[Formula 1]

wherein D is selected from Formula 2, and A is selected from Formula 3, wherein each of L1 and L2 is substituted or non-substituted benzene, and each of n1 and n2 is 0 (zero) or 1:

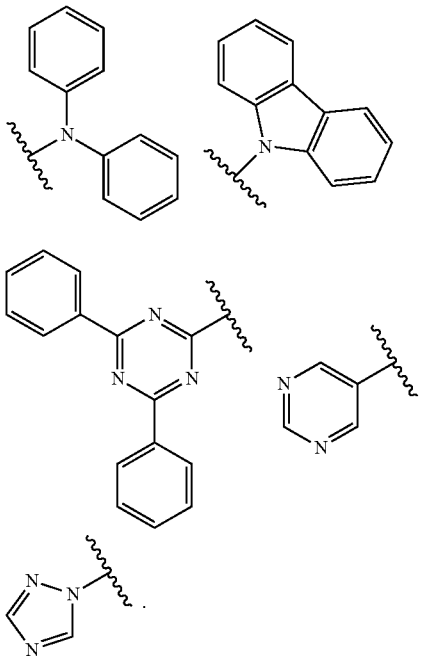

[Formula 2]

[Formula 3]

9. The organic light emitting diode according to claim 8, wherein the organic emitting layer includes a hole injection layer (HIL), a hole transporting layer (HTL), an emitting material layer (EML), an electron transporting layer (ETL), and an electron injection layer (EIL), and
wherein at least one of the HIL, the HTL, the EML, the ETL, and the EIL includes the space-through charge transfer compound.

10. The organic light emitting diode according to claim 8, wherein a difference between a singlet energy of the space-through charge transfer compound and a triplet energy of the space-through charge transfer compound is less than 0.3 eV.

11. The organic light emitting diode according to claim 8, wherein the organic emitting layer further includes a host, and the space-through charge transfer compound is used as a dopant.

12. The organic light emitting diode according to claim 11, wherein a difference between a highest occupied molecular orbital (HOMO) of the dopant and a HOMO of the host or a difference between a lowest unoccupied molecular orbital (LUMO) of the host and a LUMO of the dopant is less than 0.5 eV.

13. The organic light emitting diode according to claim 8, wherein the organic emitting layer further includes a dopant, and the space-through charge transfer compound is used as a host.

14. The organic light emitting diode according to claim 8, wherein the organic emitting layer further includes a host and a first dopant, and the space-through charge transfer compound is used as a second dopant, and
wherein a triplet energy of the second dopant is smaller than a triplet energy of the host and larger than a triplet energy of the first dopant.

15. A display device, comprising:
a substrate;
an organic light emitting diode on the substrate and including a first electrode, a second electrode facing the first electrode, and an organic emitting layer between the first electrode and the second electrode, the organic emitting layer including a space-through charge transfer compound;
an encapsulation film on the organic light emitting diode; and
a cover window on the encapsulation film,
wherein the space-through charge transfer compound includes a paracyclophane core, an electron donor moiety selected from the group consisting of carbazole and diphenyl amine, and an electron acceptor moiety selected from the group consisting of pyrimidine, diphenyltriazine, and triazole,
wherein the electron donor moiety and the electron acceptor moiety are indirectly or directly combined to the paracyclophane core with or without a linker, respectively, and
wherein the organic emitting layer further includes a host, and the space-through charge transfer compound is used as a dopant.

16. A display device, comprising:
a substrate; and
an organic light emitting diode on the substrate and including a first electrode, a second electrode facing the first electrode, and an organic emitting layer between the first electrode and the second electrode, the organic emitting layer including a space-through charge transfer compound of Formula 1,

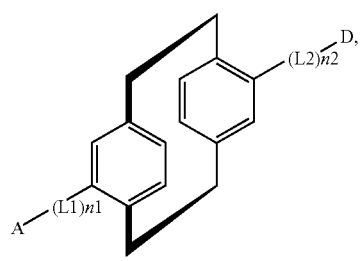

[Formula 1]

wherein D is selected from Formula 2, and A is selected from Formula 3, wherein each of L1 and L2 is substituted or non-substituted benzene, and each of n1 and n2 is 0 (zero) or 1:

[Formula 2]
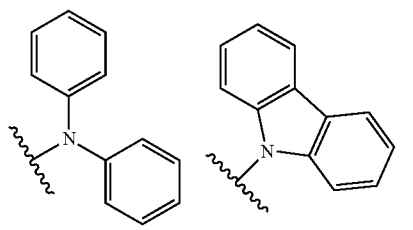
[Formula 3]
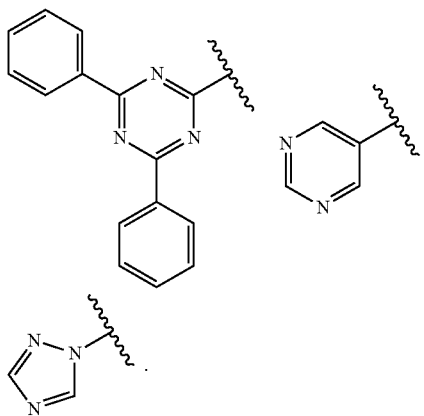
\* \* \* \* \*